United States Patent [19]

Brunetti et al.

[11] Patent Number: 5,079,231
[45] Date of Patent: Jan. 7, 1992

[54] IMMUNOSTIMULATING PEPTIDES, A PROCESS FOR THEIR PREPARATION AND PHARMACEUTICAL COMPOSITIONS CONTAINING THEM

[75] Inventors: Brunetto Brunetti; Marco Prada, both of Milan, Italy

[73] Assignee: Ellem Industria Farmaceutica S.p.A., Milan, Italy

[21] Appl. No.: 384,327

[22] Filed: Jul. 24, 1989

[30] Foreign Application Priority Data

Jul. 29, 1988 [IT] Italy ................................ 21556 A/88

[51] Int. Cl.$^5$ .......................... A61K 37/02; C07K 7/06
[52] U.S. Cl. ...................................... 514/15; 514/017; 530/330; 530/328
[58] Field of Search ...................... 530/330; 514/11, 18

[56] References Cited

U.S. PATENT DOCUMENTS

| | | | |
|---|---|---|---|
| 4,505,853 | 3/1985 | Goldstein et al. | 530/330 |
| 4,650,788 | 3/1987 | Kessler et al. | 514/11 |
| 4,874,844 | 10/1989 | Brunetti et al. | 514/18 |
| 4,929,601 | 5/1990 | Brunetti et al. | 514/18 |

Primary Examiner—Lester L. Lee
Assistant Examiner—S. G. Marshall
Attorney, Agent, or Firm—Bucknam and Archer

[57] ABSTRACT

The peptides of formula I

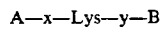

$$A-x-Lys-y-B \qquad I$$

in which:

A is H, a tripeptide of formula Arg-Ala-Arg or an hexapeptide of formula Glu-Lys-Arg-Arg-Ala-Arg
x and y, different one from the other, are an arginine (Arg) or a glutamic acid (Glu) residue;
B is OH or a tripeptide Arg-Ala-Arg with the proviso that when A is hydrogen and x is ARg, B is different from OH comprising the steps of:
 a) binding the Boc-protected carboxyterminal aminoacid to a suitable resin;
 b) reacting the other Boc-protected aminoacids with the resin-bound carboxyterminal aminoacid in the desired sequence;
 c) removing the protecting groups and releasing the so obtained peptides from the resin, have valuable pharmacological properties as immunostimulating agents.

4 Claims, No Drawings

IMMUNOSTIMULATING PEPTIDES, A PROCESS FOR THEIR PREPARATION AND PHARMACEUTICAL COMPOSITIONS CONTAINING THEM

The present invention concerns peptides having general formula

A—x—Lys—y—B   I in which:
- A is H, a tripeptide of formula Arg-Ala-Arg or an hexapeptide of formula Glu-Lys-Arg-Arg-Ala-Arg
- x and y, different one from the other, are an arginine (Arg) or a glutamic acid (Glu) residue;
- B is OH or a tripeptide Arg-Ala-Arg with the proviso that when A is hydrogen and x is Arg, B is different from OH.

The aminoacids composing the peptides .of the invention may be either of the natural, L-series or of the D-series or a racemic mixture of the two said series.

Preferred peptides of the invention are those wherein either A or B are Arg-Ala-Arg, x is Arg and y is Glu.

Another preferred group of peptides of the invention is that having A=Glu-Lys-Arg-Arg-Ala-Arg, x is Glu and y is Arg. A further preferred group of peptides is that having both A and B=Arg-Ala-Arg whereas x and y are independently Arg or Glu.

The aminoacids are preferably selected from the L-forms even though D- or DL aminoacids, especially D-Ala or D-glutamic acid, may also be considered.

The invention refers also to the process for the preparation of said peptides as well as to their use as immunostimulant agents.

In the following disclosure the following abbreviations are used:
- Ala=L-alanine
- Arg=L-arginine
- Boc=butyloxycarbonyl
- D-Ala=D-alanine
- Glu=L-glutamic acid
- D-Glu=D-glutamic acid
- Lys=L-lysine
- $N^g$=substitution on the guanidinic nitrogen of Arg.

The tripeptide Arg-Ala-Arg is known from the Italian patent application n. 20027 A/86 of 9.04.1986: it is endowed with immunostimulating activity and it is able to. enhance both the T-cells maturation and functional abilities.

Also the Arg-Lys-Glu tripeptide (splenotritin) corresponding to the 32-34 fragment of splenopoietin, a polypeptide hormone extracted from the bovine spleen and originally referred to as thymopoietin III because of its high affinity with thymopoietins I and II isolated from thymus, has immunostimulating properties, involving the maturation and functionality of T-lymphocytes (Italian patent application n. 20026 A/86 of 9.04.1986; Diezel W. et al.: Biomed. Biochim. Acta 45, 1349, 1986).

Similarly, the peptide Arg-Lys-Asp, differing from Arg-Lys-Glu only in the C-terminal aminoacidic residue, displays a similar behaviour (EP-A-0067425) as well as Arg-Gly-Asp, disclosed in the Italian patent application n. 21575 A/87 of 4.08.1987.

The peptides according to the invention proved to be active as immunostimulating agents, being effective in in vitro experimental models in promoting the maturation of murine immature T-lymphocytes and in enhancing the functionality of human T-cells. The peptides are able to restore the immune function in nude athymic mice, when administered for 5 days, 2 or 6 weeks by oral or i.p. route.

Like Arg-Ala-Arg and Arg-Lys-Glu, also the peptides of the present invention are stable to the in vitro simulated gastric juice.

Analogously to the two peptides above mentioned, whose stability in the simulated gastric juice is related to the activity after oral administration, it has been demonstrated that also the peptides of the invention are endowed with immunostimulating activity both after oral administration and after parenteral administration.

This fact represents a remarkable advantage in the therapeutic use, with particular reference to the treatment of children and of other patients who do not tolerate the parenteral administration and also as a consequence of a better patient's compliance to the prescribed therapy.

According to what above described, the compounds of the invention have such features so as to make them, particularly useful in the clinical practice for the therapy both of primary and secondary deficiencies.

The clinical utilities of immunostimulating compounds are described for instance in Immun. Lett. Vol. 16, 363, 1987, JAMA Vol. 258, 3005, 1987 and Drug Discovery and Development, Eds. Williams M. and Malick J.B., Humana 1987, p. 227, which are herein incorporated by reference.

For the intended use, the peptides of the invention may be administered either alone or in admixture with pharmaceutically acceptable carrier, in suitable pharmaceutical formulations which are a further object of the invention.

Examples of said formulations, which may be prepared using well known methods and excipients, such as those described in "Remington's Pharmaceutical Sciences Handbook", Mack Pub.Co., N.Y. USA., are tablets, capsules, syrups, and the like for the oral administration whereas for the parenteral administration suitable forms are sterile solutions or suspensions in acceptable liquids, implants, etc. The preferred dosage form is a unit dose comprising from about 0.1 to about 500 mg of a peptide of formula I or the equivalent of a pharmaceutically acceptable salt thereof, such as acetate, hydrochloride, trifluoroacetate, sulfate salts.

The posology will depend on several factors such as type and seriousness of the pathologic conditions to be treated, patient's weight and sex, etc. and will be easily determined by the skilled practitioner. Generally one to four administrations a day will be prescribed.

The peptides I are prepared according to conventional methods, well known in peptide chemistry, such as solid state synthesis on resins. , The following non limitative examples are given as a further illustration of the invention.

EXAMPLE 1

General Procedure for the Solid Phase Synthesis of Peptides 1. Preparation of resins substituted with Boc-aminoacids Chloromethylated polystyrene (1% crosslinked; 200-400 mesh) is swelled in dimethylformamide (DMF) (about 8-10 ml per g of resin), then treated with the Boc-aminoacid (1 mole per g of resin), followed by potassium fluoride (2 moles per g of resin). A small amount of solvent (5-10 ml) is then distilled off under vacuum after which the mixture is heated to 80°-100° C.

for 16–18 hours. While cooling, the resin is filtered, washed with DMF, DMF:H$_2$O 1:1, H$_2$O ethanol, CH$_2$Cl$_2$ and methanol and then dried under vacuum. Substitution (calculated by the weight increase)=0-.4–0.6 moles per g.

2. General synthetic procedure

The suitable amount of resin substituted with the C-terminal Boc-aminoacid in the desired sequence is sequentially treated at room temperature (20°–25° C.) with:
a) CH$_2$Cl$_2$
b) 50% CF$_3$COOH:CH$_2$Cl$_2$ (v/v)
c) 50% CF$_3$COOH:CH$_2$Cl$_2$ for 25'
d) CH$_2$Cl$_2$ (3 times)
e) isopropanol
f) 10% triethylamine:CH$_2$Cl$_2$ (v/v) (twice)
g) CH$_2$Cl$_2$
h) methanol (twice)
i) CH$_2$Cl$_2$ (twice)

The contact time for each treatment is 3–5 minutes except treatment c).
About 10–15 ml of solvent or of solvent reagent mixture are used per g of resin in each step.

j) The resin is stirred with a solution of the suitably protected, last but one Boc-aminoacid of the desired sequence (3 equivalents) in CH$_2$Cl$_2$, dicyclohexylcarbodiimide (3 equivalents) is then added thereto in CH$_2$Cl$_2$. The reaction time is at least 2–4 hours and it may last overnight (16–18 hours).

The resin to which the peptide is bound is filtered and washed with CH$_2$Cl$_2$, methanol and CH$_2$Cl$_2$ and the synthesis completion is checked by the ninhydrine reaction. If the synthesis is incomplete, the same aminoacid is coupled again using half amounts of the reagents. The cycle is repeated for each aminoacid of the sequence, until this is completed.

After removal of the N-terminal Boc group, the resin to which the peptide is bound is carefully washed and dried under vacuum.

The peptide is detached from the resin and contemporaneously deprotected by treatment with anhydrous hydrofluoric acid (about 10 ml per g of resin) containing anisole (10% v/v) for 1 h at 0° C.

After evaporation of hydrofluoric acid under reduced pressure, the crude peptide is extracted by washing the resin with diluted aqueous acetic acid and the product is isolated by lyophilization.

3. Purification of the crude peptide

The crude peptides may be purified by reverse phase preparative HPLC using silanized silica with C18 chain with, for instance, a Waters Prep 500 instrument. Using a 5×30 cm column, equilibrated with the suitable aqueous buffer, such as aqueous 0,1% trifluoroacetic acid, the crude peptide (about 2 g) is applied on the column and eluted with a gradient containing increasing amounts of acetonitrile. The fractions are checked by analytical HPLC and those containing the product at the desired purity degree (>95%) are collected and lyophilized. Finally, the purified product is transformed in the desired salt by treatment with the desired salt form of an ion-exchange resin.

SYNTHESIS OF ARG-LYS-GLU-ARG-ALA-ARG

The peptide is synthesized according to the above described general method, starting from the resin containing Boc-N$^g$-tosyl-L-arginine (5 g; substitution: 0.5–0.6 moles per g) and adding the following aminoacids:
1. Boc-L-alanine
2. Boc-N$^g$-tosyl-L-arginine (in DMF)
3. Boc-γ-benzyl-L-glutamic acid
4. Boc-epsilon-benzyloxycarbonyl-L-lysine
5. Boc-N$^g$-tosyl-L-arginine (in DMF)

SYNTHESIS OF ARG-LYS-GLU-ARG-D-ALA-ARG

The resin substituted with Boc-N$^g$-tosyl-L-arginine (6 g; substitution about 0.5 moles per gram) is sequentially treated with the following aminoacids, according to the above disclosed general protocol:
1. Boc-D-alanine
2. Boc-N$^g$-tosyl-L-arginine (in DMF)
3. Boc-γ-benzyl-L-glutamic acid
4. Boc-epsilon-2- chlorobenzyloxycarbonyl-L-lysine
5. Boc-N$^g$-tosyl-L-arginine (in DMF)

SYNTHESIS OF ARG-ALA-ARG-ARG-LYS-GLU

The peptide is synthesized according to the above described general method, starting from the resin containing Boc- -benzyl-L-glutamic acid (5 g; substitution: 0.5–0.6 moles per g) and adding the following aminoacids:
1. Boc-epsilon-benzyloxycarbonyl-L-lysine
2. Boc-N$^g$-tosyl-L-arginine (in DMF)
3. Boc-N$^g$-tosyl-L-arginine (in DMF)
4. Boc-L-alanine
5. Boc-N$^g$-tosyl-L-arginine (in DMF)

SYNTHESIS OF ARG-D-ALA-ARG-ARG-LYS-GLU

The resin substituted with Boc-γ-benzyl-L-glutamic acid (6 g; substitution: about 0.5 moles per g) is treated with the following aminoacid derivatives, according to the above disclosed general method:

1. Boc-epsilon-2-chlorobenzyloxycarbonyl-L-lysine
2. Boc-N$^g$-tosyl-L-arginine (in DMF)
3. Boc-N$^g$-tosyl-L-arginine (in DMF)
4. Boc-D-alanine
5. Boc-N$^g$-tosyl-L-arginine (in DMF)

SYNTHESIS OF ARG-ALA-ARG-ARG-LYS-GLU-ARG-ALA-ARG

The peptide is synthesized according to the above described general method, starting from the resin containing Boc-N$^g$-tosyl-L-arginine (5 g; substitution: about 0.5 moles per g) and adding the following aminoacids:
1. Boc-L-alanine
2. Boc-N$^g$-tosyl-L-arginine (in DMF)
3. Boc-γ-benzyl-L-glutamic acid
4. Boc-epsilon-2-chlorobenzyloxycarbonyl-L-lysine
5. Boc-N$^g$-tosyl-L-arginine (in DMF)
6. Boc-N$^g$-tosyl-L-arginine (in DMF)
7. Boc-L-alanine
8. Boc-N$^g$-tosyl-L-arginine (in DMF)

SYNTHESIS OF GLU-LYS-ARG AND RELATED PEPTIDES

Boc-N$^g$-Tosyl-L-arginine (substitution approx 0.6 mmole per gram; 20 grams) was treated with the following aminoacid derivative, using the general protocol described previously:
1. Boc-2-chlorobenzyloxycarbonyl
2. Boc-γ-benzyl-L-glutamic acid The previous procedure was repeated using D-glutamic acid instead of L-glutamic acid. Using the same procedures, the following peptides were also prepared:

Arg-Ala-Arg-Glu-Lys-Arg
Glu-Lys-Arg-Arg-Ala-Arg
Glu-Lys-Arg-Arg-Ala-Arg-Glu-Lys-Arg

EXAMPLE 2

Chemical Characteristics

The date hereinbelow reported refer only to a single batch of each peptide and should not be intended in limitative sense.

ARG-LYS-GLU-ARG-ALA-ARG

Molecular weight: 815,0
Aspect: white powder

| Aminoacid analysis | | |
|---|---|---|
| Aminoacid | calcd. | found |
| Alanine | 1.00 | 0.97 |
| Lysine | 1.00 | 1.00 |
| Glutamic acid | 1.00 | 1.00 |
| Arginine | 3.00 | 3.05 |

Peptide content: 80.9% (+/−0.3%)
Peptide purity: 98,62%
HPLC: the analysis was carried out using the following methods
Eluents:
   A = NaH2PO4 25mM + NaClO4 60mM, pH 2,9 with H3PO4
   B = 60% CH3CN + 40% H20
Gradient: from 100% of A linear increment of B (1% min)
Column: Ultrasphere ODS 5 μm, 4.6mm×25 cm (Beckman)
Flow-rate: 0.9 ml/min.
Wavelength: 210 nm
Retention time: 21'

ARG-LYS-GLU-ARG-D-ALA

Molecular weight: 815,0
Aspect: white powder

| Aminoacid analysis | | |
|---|---|---|
| Aminoacid | calcd. | found |
| Alanine | 1.00 | 1.03 |
| Glutamic acid | 1.00 | 1.01 |
| Lysine | 1.00 | 1.00 |
| Arginine | 3.00 | 2.87 |

Peptide content: 65.9% (+/−3.0%)
Peptide purity: 99.2%
HPLC: the analysis was carried out using the following methods
Eluents:
   A = NaH2PO4 25mM + NaClO4 70mM, pH 3.0 with H3PO4
   B = 60% CH3CN + 40% H20
Gradient: from 0% to 25% of B in 30 min.
Column: Deltapak-C18 15 μm, 3.9mm×30 cm
Flow-rate: 0.7 ml/min.
Wavelength: 210 nm
Retention time: 22'

ARG-ALA-ARG-ARG-LYS-GLU

Molecular weight: 815.0
Aspect: white powder

| Aminoacid analysis | | |
|---|---|---|
| Aminoacid | calcd. | found |
| Alanine | 1.00 | 1.01 |
| Glutamic acid | 1.00 | 1.00 |
| Lysine | 1.00 | 0.99 |
| Arginine | 3.00 | 3.03 |

Peptide content: 73,5% (+/−1,0%)
Peptide purity: 99.81%
HPLC: the analysis was carried out using the following methods
Eluents:
   A = NaH2PO4 25mM + NaClO4 60mM, pH 2.9 with H3PO4
   B = 60% CH3CN + 40% H20
Gradient from 100% of A linear increment of B (1%/min)
Column: Ultrasphere ODS 5 μm, 4.6mm×25 cm (Beckman)
Flow-rate: 0.9 ml/min.
Wavelength: 210 nm
Retention time: 20'

ARG-D-ALA-ARG-ARG-LYS-GLU

Molecular weight: 815,0
Aspect: white powder

| Aminoacid analysis | | |
|---|---|---|
| Aminoacid | calcd. | found |
| Alanine | 1.00 | 0.98 |
| Glutamic acid | 1.00 | 1.00 |
| Lysine | 1.00 | 1.02 |
| Arginine | 3.00 | 2.96 |

Peptide content: 74,0% (+/−2,7%)
Peptide purity: 99.1%
HPLC: the analysis was carried out using the following methods
Eluents:
   A = NaH2PO4 25mM + NaClO4 70mM, pH 3,0 with H3PO4
   B = 60% CH3CN + 40% H20
Gradient: from 0% to 25% of B in 30 min.
Column: Deltapak-C18 15 μm, 3,9mm×30 cm
Flow-rate: 0,7 ml/min.
Wavelength: 210 nm
Retention time: 23'

ARG-ALA-ARG-ARG-LYS-GLU-ARG-ALA-ARG

Molecular weight: 1198,5
Aspect: white powder
Aminoacid analysis

| Aminoacid | calcd. | found |
|---|---|---|
| Alanine | 2.00 | 2.01 |
| Glutamic acid | 1.00 | 0.99 |
| Lysine | 1.00 | 1.03 |
| Arginine | 5.00 | 4.91 |

Peptide content: 69,6% (+/−7.2%)
Peptide purity: 99.2%

HPLC: the analysis was carried out using the following methods

Eluents:
  A = NaH2PO4 25mM + NaClO4 70mM, pH 3,0 with H3PO4
  B = 60% CH3CN + 40% H20

Gradient: from 0% to 30% of B in 25 min.
Column: Deltapak-C18 15 μm, 3,9mm × 30 cm
Flow-rate: 0.7 ml/min.
Wavelength: 210 nm
Retention time: 26'

GLU-LYS-ARG

Molecular weight: 431,5
Aspect: white powder

| Aminoacid | Aminoacid analysis | |
|---|---|---|
| | calcd. | found |
| Glutamic acid | 1.00 | 1.06 |
| Lysine | 1.00 | 0.89 |
| Arginine | 1.00 | 0.94 |

Peptide content: 71,2% (+/−3%)
Peptide purity: >97%

D-GLU-LYS

Molecular weight: 431.5
TLC: Butanol/AcOH/H2O 4/2/2 Rf=0.2
Peptide content: 81.0%

| Aminoacid | Aminoacid analysis | |
|---|---|---|
| | calcd. | found |
| Glutamic acid | 1.00 | 1.00 |
| Lysine | 1.00 | 1.03 |
| Arginine | 1.00 | 0.96 |

ARG-ALA-ARG-GLU-LYS-ARG

Molecular weight: 815

| Aminoacid | Aminoacid analysis | |
|---|---|---|
| | calcd. | found |
| Arginine | 3.00 | 3.10 |
| Alanine | 1.00 | 0.90 |
| Glutamic acid | 1.00 | 1.02 |
| Lysine | 1.00 | 0.96 |

Peptide content: 74,4%
Peptide purity: 89.6%
RP-TLCL: H2O/CH3CN/TFA 80/20/0.1 Rf=0,8

GLU-LYS-ARG-ARG-ALA-ARG-GLU-LYS-ARG

Molecular weight: 1228.4

| Aminoacid | Aminoacid analysis | |
|---|---|---|
| | calcd. | found |
| Glutamic acid | 1.00 | 1.11 |
| Lysine | 1.00 | 1.00 |
| Arginine | 3.00 | 0.99 |
| Alanine | 1.00 | 2.99 |

Peptide content: 74.3%
Peptide purity: 95%

GLU-LYS-ARG-ARG-ALA-ARG-GLU-LYS-ARG

Molecular weight: 1228,4
RP-TLC: H2O/CH3CN/TFA 80/20/0,1 Rf=0.8

| Aminoacid | Aminoacid analysis | |
|---|---|---|
| | calcd. | found |
| Glutamic acid | 2.00 | 2.00 |
| Alanine | 1.00 | 1.04 |
| Lysine | 2.00 | 1.94 |
| Arginine | 4.00 | 3.97 |

Peptide content: 83%
Peptide purity: >95%

EXAMPLE 3

Biological Characteristics

Resistance to the in vitro simulated gastric ambient

The hexapeptides Arg-Lys-Glu-Arg-Ala-Arg and Arg-Ala-Arg-Arg-Lys-Glu are stable at 37° C. for 3 hours in in vitro simulated gastric ambient using the gastric simulated juice USP XXl (HCl + pepsin).

In vitro induction of Thy 1.2 antigen in splenocytes from nude mice

Spleen cells from congenitally athymic nude mice have been used, after incubation for 18 hours with different peptide concentrations. The induction of the Thy 1.2 marker has been evaluated by direct immunofluorescence, by means of fluorescence microscope.

The results, reported in the table, show that the hexapeptides Arg-Lys-Glu-Arg-Ala-Arg and Arg-Ala-Arg-Arg-Lys-Glu are able to induce the appearance of the Thy 1.2 marker, with a bell-shaped dose-response relationship curve, as it is typical for immunostimulating compounds.

| PEPTIDE CONCEN- TRATION μg/ml | % Thy 1.2+ cells | | | |
|---|---|---|---|---|
| | ARG—LYS—GLU—ARG—ALA—ARG | | ARG—ALA—ARG—ARG—LYS—GLU | |
| | test 1 | test 2 | test 1 | test 2 |
| 0 | 5 | 9 | 5 | 9 |
| 0,0001 | 7 | 12 | 5 | 10 |
| 0,001 | 10 | 15 | 8 | 18 |
| 0,01 | 18 | 24 | 14 | 22 |
| 0,1 | 28 | 34 | 20 | 30 |
| 1 | 32 | 39 | 27 | 32 |
| 10 | 34 | 40 | 28 | 32 |
| 50 | 31 | 31 | 28 | 25 |
| 100 | 20 | 24 | 17 | 14 |

RNA synthesis in human T-lymphocytes stimulated in vitro with phythohemagglutinin Human T-lymphocytes incubated in vitro for 24 h, in the presence of 0,5% phytohemagglutinin (PHA) and of different peptide concentrations, have been analyzed for the RNA synthesis by means of 3H-uridine labelling. The results, disclosed in the following tables, show that the tripeptide Glu-Lys-Arg, the hexapeptides Arg-Ala-Arg-Arg-Lys-Glu, Arg-Lys-Glu-Arg-Ala-Arg, Arg-D-Ala-Arg-Arg-Lys-Glu, Arg-Lys-Glu-Arg-D-Ala-Arg and the nonapeptide Arg-Ala-Arg-Arg-Lys-Glu-Arg-Ala-Arg are able to stimulate the RNA synthesis of PHA activated human lymphocytes.

μg/ml of Glu-Lys-Arg and the RNA synthesis was evaluated by the 3H uridine incorporation.

As shown in the Table, also in this case the peptide is able to enhance the RNA synthesis of the already activated cells.

| PEPTIDE | 3H-URIDINE INCORPORATION (cpm) | |
|---|---|---|
| | X ± SE | Δ % |

| PEPTIDE CONCENTRATION | 3H-URIDINE INCORPORATION (cpm) | | | |
|---|---|---|---|---|
| | ARG—LYS—GLU—ARG—ALA—ARG | | ARG—ALA—ARG—ARG—LYS—GLU | |
| mcg/ml | X* +/− S.E. | Δ% | X* +/− S.E. | Δ% |
| 0 | 13748 1806 | — | 13748 1806 | — |
| 0.0001 | 14337 1649 | +4 | 13490 1405 | +2 |
| 0.001 | 15471 1793 | +13 | 14395 1704 | +5 |
| 0.01 | 17851 2248 | +30 | 17285 1602 | +26 |
| 0.1 | 21320 2167 | +55 | 19939 2027 | +45 |
| 1 | 20403 1429 | +48 | 18144 1729 | +32 |
| 10 | 20147 1338 | +47 | 16628 1371 | +21 |
| 100 | 16194 702 | +18 | 14397 1044 | +5 |

*mean of 6 values

| | RNA SYNTHESIS (MEAN OF 5 TESTS) | | | | | |
|---|---|---|---|---|---|---|
| CONCENTRATION | ARG—ALA—ARG—ARG—LYS—GLU—ARG—ALA—ARG c.p.m. | | ARG—LYS—GLU—ARG—D—ALA—ARG c.p.m. | | ARG—D—ALA—ARG—ARG—LYS—GLU c.p.m. | |
| mcg/ml | X ± S.E. | Δ % | X ± S.E. | Δ % | X ± S.E. | Δ % |
| 0 | 3835 108 | — | 3835 108 | — | 3835 108 | — |
| 0.0001 | 3606 298 | −6 | 4073 318 | +6 | 3970 416 | +4 |
| 0.001 | 3855 238 | +1 | 4586* 479 | +20 | 4023 206 | +5 |
| 0.01 | 4456 266 | +16 | 5774** 657 | +51 | 4775* 220 | +25 |
| 0.1 | 4623** 200 | +21 | 5526** 314 | +44 | 5016** 357 | +31 |
| 1 | 4747 581 | +24 | 5450** 272 | +42 | 4369 393 | +14 |
| 10 | 4986* 445 | +30 | 4848 473 | +26 | 4569 309 | +19 |

*P 0,05
**P 0,01

| GLU—LYS—ARG CONCENTRATION | 3H-URIDINE INCORPORATION (cpm) | |
|---|---|---|
| μg/ml | X (± SE) | Δ % |
| 0 | 2866 (517) | — |
| 0.01 | 3489 (574) | + 22 |
| 0.1 | 5149 (545)x* | + 80 |
| 1 | 7883 (311)x* | + 175 |
| 10 | 3609 (1486) | + 26 | x* = p < 0.01

In vitro synthesis of RNA by human lymphocytes activated with anti -T3 monoclonal antibody Human T-lymphocytes activated in vitro with an activator more specific than PHA, i.e. the anti-T3monoclonal antibody (1.56 ng/ml), were incubated with 1

| CONTROLS | 1155 115 | — |
|---|---|---|
| GLU—LYS—ARG | 3657 406 | + 217 |

In vitro DNA synthesis in human T-lymphocytes stimulated by PHA

Human T-lymphocytes incubated in vitro for 72 h in the presence of 0.5% PHA and of different peptide concentrations were analyzed for the DNA synthesis (proliferation) by 3H-thymidine labelling.

The results, reported in the following tables, show that the peptides are able to stimulate the DNA synthesis.

| PEPTIDE CONCEN-TRATION μg/ml | 3H-THYMIDINE INCORPORATION (cpm) | | | |
|---|---|---|---|---|
| | ARG—LYS—GLU—ARG—ALA—ARG | | ARG—ALA—ARG—ARG—LYS—GLU | |
| | X* +/− S.E. | Δ % | X* +/− S.E. | Δ % |
| 0 | 59399 4346 | — | 59399 4346 | — |
| 0.0001 | 57477 5346 | − 3 | 59758 4762 | − 1 |
| 0.001 | 61682 4559 | + 4 | 62751 4213 | + 6 |
| 0.01 | 69164 1601 | + 16 | 68755 2556 | + 16 |
| 0.1 | 76821 3572 | + 29 | 77401 3023 | + 30 |
| 1 | 80920 3935 | + 36 | 78390 4063 | + 32 |
| 10 | 74648 6772 | + 26 | 77983 5975 | + 31 |
| 100 | 62863 7050 | + 6 | 69780 6146 | + 17 |

*mean of 5 values

| GLU—LYS—ARG CONCENTRATION | 3H-THYMIDINE INCORPORATION (cpm) | |
|---|---|---|
| | X (± SE) | Δ % |
| 0 | 10140 (2205) | — |
| 0.01 | 20648 (4456) | + 104 |
| 0.1 | 18660 (6032) | + 84 |
| 1 | 22332 (7014) | + 120 |
| 10 | 23241 (1209) | + 129 |

In vitro stimulation of ConA-induced proliferation
Peripheral blood mononuclear cells (PBMC), obtained from health volunteers, were incubated with ConA in order to evaluate the proliferation as labeled thymidine uptake.

| In vitro stimulation of the proliferation induced by 0.325 mcg/ml of ConA | | | |
|---|---|---|---|
| | | c.p.m. (mean ± S.E.) | |
| TREATMENT | PEPTIDE CONC. (mcg/ml) | c.p.m. | Δ % |
| PBMC | — | 2582 ± 658 | — |
| PBMC + ConA | — | 46240 ± 3002 | — |
| ARG—ALA—ARG—ARG—LYS—GLU | 0.1 | 47455 ± 5981 | +3 |
| ARG—ALA—ARG—ARG—LYS—GLU | 1.0 | 52516 ± 974 | +14 |
| ARG—ALA—ARG—ARG—LYS—GLU | 10.0 | 61329 ± 859 | +33 |
| ARG—ALA—ARG—ARG—LYS—GLU—ARG—ALA—ARG | 0.1 | 52125 ± 416 | +13 |
| ARG—ALA—ARG—ARG—LYS—GLU—ARG—ALA—ARG | 1.0 | 54704 ± 10827 | +18 |
| ARG—ALA—ARG—ARG—LYS—GLU—ARG—ALA—ARG | 10.0 | 57256 ± 12729 | +24 |

| CONCENTRATION mcg/ml | DNA SYNTHESIS (MEAN OF 5 TESTS) | | | | | |
|---|---|---|---|---|---|---|
| | ARG—ALA—ARG—ARG—LYS—GLU—ARG—ALA—ARG c.p.m. | | ARG—LYS—GLU—ARG—D—ALA—ARG c.p.m. | | ARG—D—ALA—ARG—ARG—LYS—GLU c.p.m. | |
| | X ± S.E. | Δ % | X ± S.E. | Δ % | X ± S.E. | Δ % |
| 0 | 22642 3688 | — | 22642 3688 | — | 22642 3688 | — |
| 0.0001 | 21369 3009 | −6 | 22454 2943 | −1 | 21904 3684 | −3 |
| 0.001 | 21876 3076 | −3 | 22916 2924 | +1 | 24915 4734 | +10 |
| 0.01 | 23715 3998 | +5 | 26613 3639 | +18 | 27658* 4827 | +22 |
| 0.1 | 27960 3394 | +23 | 30044 3824 | +33 | 28460 4108 | +26 |
| 1 | 29866 3840 | +32 | 29482 4671 | +30 | 25956 3841 | +14 |
| 10 | 27400 3878 | +21 | 26414 3727 | +17 | 24568 3884 | +9 |

| In vitro stimulation of the proliferation induced by 0.625 mcg/ml of ConA | | | |
|---|---|---|---|
| | | c.p.m. (mean ± S.E.) | |
| TREATMENT | PEPT. (mcg/ml) | c.p.m. | % |
| PBMC | — | 950 ± 276 | — |
| PBMC + ConA | — | 67890 ± 5093 | — |
| GLU—LYS—ARG | 0.01 | 88280 ± 17106 | +30 |
| GLU—LYS—ARG | 0.1 | 88734 ± 12731 | +31 |
| GLU—LYS—ARG | 1.0 | 79319 ± 4435 | +17 |
| GLU—LYS—ARG | 10.0 | 72666 ± 19568 | +7 |
| ARG—LYS—GLU—ARG—D—ALA—ARG | 0.1 | 73582 ± 4843 | +8 |
| ARG—LYS—GLU—ARG—D—ALA—ARG | 1.0 | 96997 ± 10762 | +43 |
| ARG—LYS—GLU—ARG—D—ALA—ARG | 10.0 | 93568 ± 7191 | +38 |

-continued

| In vitro stimulation of the proliferation induced by 0.625 mcg/ml of ConA | | | |
|---|---|---|---|
| | | c.p.m. (mean ± S.E.) | |
| TREATMENT | PEPT. (mcg/ml) | c.p.m. | % |
| ARG—ALA—ARG—ARG—LYS—GLU | 0.1 | 72178 ± 7076 | +6 |
| ARG—ALA—ARG—ARG—LYS—GLU | 1.0 | 70260 ± 6782 | +3 |
| ARG—ALA—ARG—ARG—LYS—GLU | 10.0 | 84390 ± 345 | +24 |

Stimulation of the in vitro IL-2, BCGF and γ-IFN production by PHA activated cells Human T-lymphocytes have been incubated with PHA in the presence or in the absence of 1 μg of peptides, for 24 h in the case of IL-2, 72 h for BCGF and 36 h for gamma-interferon (γ/IFN).

The supernatants were collected, filtered (0.2 μm) and assayed for the activity of IL 2 or BCGF by addition at different concentrations to fresh T-lymphocytes or to B-cells coming from long term-cultures. The proliferative activity of said cells, depending on the presence of the corresponding growth-factor, has been evaluated by 3H-thymidine incorporation.

The γ-interferon activity in the supernatant has been evaluated by an ELISA kit (AMGEN). The results, reported in the subsequent tables, show a stimulation effect on the lymphokine production by the peptides.

| | PRODUCTION OF IL-2 (cpm) | | | | |
|---|---|---|---|---|---|
| SUPER-NATANT | CONTR | ARG—LYS—GLU—ARG—ALA—ARG | | ARG—ALA—ARG—ARG—LYS—GLU | |
| % | X* +/− S.E. | X* +/− S.E. | Δ % | X* +/−S.E. | Δ % |
| 3.125 | 2366 | 4482 | +90 | 4601 | +94 |
| | 395 | 625 | | 570 | |
| 6.25 | 4528 | 12813 | +183 | 15053 | +232 |
| | 802 | 2925 | | 3303 | |
| 12.5 | 8132 | 18938§ | +128 | 21682§§ | +161 |
| | 1522 | 1760 | | 1612 | |
| 25 | 15616 | 24144§ | +55 | 28808§§ | +84 |
| | 1823 | 1753 | | 1155 | |
| 50 | 19166 | 26535 | +38 | 32777§ | +71 |
| | 2459 | 1400 | | 2054 | |

*mean of 4 values
§P < 0.05;
§§P < 0.01

| | PRODUCTION OF BCGF (cpm) | | | | |
|---|---|---|---|---|---|
| SUPER-NATANT | CONTR | ARG—LYS—GLU—ARG—ALA—ARG | | ARG—ALA—ARG—ARG—LYS—GLU | |
| % | X* +/− S.E. | X* +/− S.E. | Δ % | X* +/− S.E. | Δ % |
| 3.125 | 2042 | 3779 | + 85 | 4923 | + 141 |
| | 259 | 232 | | 1820 | |
| 6.25 | 4975 | 14092 §§ | + 183 | 16165 §§ | + 225 |
| | 638 | 937 | | 1569 | |
| 12.5 | 9798 | 20354 § | + 108 | 24538 §§ | + 150 |
| | 608 | 1459 | | 2356 | |
| 25 | 15605 | 23821 § | + 53 | 28953 §§ | + 86 |
| | 1458 | 1007 | | 1809 | |
| 50 | 20129 | 28966 § | + 44 | 30021 § | + 49 |
| | 1883 | 1139 | | 1814 | |

* = mean of 4 values
§ = P < 0,05;
§§ = P < 0,01

| | IL-2 PRODUCTION (cpm) | | |
|---|---|---|---|
| SUPER NATANT | CONTROL | GLU—LYS—ARG | |
| % | X ± S.E. | X ± S.E. | Δ % |
| 3.125 | 2351 | 4237 | + 80 |
| | 514 | 48 | |
| 6.2 | 4681 | 15877 | + 239 |
| | 516 | 1986 | |
| 12.5 | 11397 | 24414 | + 114 |
| | 524 | 2928 | |
| 25 | 18009 | 30912 | + 72 |
| | 2835 | 1729 | |
| 50 | 15470 | 29269 | + 89 |
| | 608 | 519 | |

| | BCGF PRODUCTION (cpm) | | |
|---|---|---|---|
| SUPER NATANT | CONTROL | GLU—LYS—ARG | |
| % | X ± S.E. | X ± S.E. | Δ % |
| 3.125 | 2803 | 4854 | + 73 |
| | 666 | 1008 | |
| 6.2 | 5653 | 13995 | + 148 |
| | 1774 | 5827 | |
| 12.5 | 10347 | 20765 | + 101 |
| | 2529 | 4873 | |

-continued

| SUPER NATANT % | BCGF PRODUCTION (cpm) | | |
|---|---|---|---|
| | CONTROL X ± S.E. | GLU—LYS—ARG X ± S.E. | Δ % |
| 25 | 18236 2609 | 26208 3473 | + 44 |
| 50 | 18868 2725 | 27983 2173 | + 48 |

| PEPTIDE | PRODUCTION OF GAMMA-INTERFERON (Units/ml) | |
|---|---|---|
| | X +/− S.E. | Δ % |
| CONTROLS | 54.5 6.2 | |
| ARG—LYS—GLU—ARG—ALA—ARG | 87.3 3.0 | + 60 |
| ARG—ALA—ARG—ARG—LYS—GLU | 112.8 3.2 | + 107 |

MITOGEN-INDUCED PROLIFERATION IN NUDE MICE TREATED ORALLY FOR 5 DAYS WITH 10 mcg/mouse OF THE PEPTIDE ARG—LYS—GLU—ARG—ALA—ARG (c.p.m.: mean ± S.E.)

| MITOGEN | % | CONTROLS | PEPTIDE | Δ % |
|---|---|---|---|---|
| PHA | 0.00 | 614 ± 234 | 630 ± 379 | + 3 |
| | 0.15 | 1109 ± 511 | 1515 ± 786 | + 37 |
| | 0.31 | 3043 ± 519 | 2965 ± 850 | + 45 |
| | 0.62 | 1230 ± 104 | 3047 ± 72 | + 145 |
| | 1.25 | 1215 ± 116 | 6034 ± 2962 | + 397 |
| | 2.50 | 954 ± 182 | 3738 ± 910 | + 292 |
| ConA | 0.00 | 839 ± 657 | 1093 ± 902 | + 30 |
| | 0.62 | 903 ± 3 | 1752 ± 83 | + 94 |
| | 1.25 | 805 ± 91 | 2152 ± 297 | + 167 |
| | 2.50 | 359 ± 143 | 1657 ± 636 | + 362 |
| | 5.00 | 197 ± 17 | 946 ± 323 | + 380 |
| | 10.00 | 286 ± 50 | 1071 ± 308 | + 274 |

PWM-INDUCED PROLIFERATION IN NUDE MICE TREATED FOR 5 DAYS WITH 10 mcg/mouse OF ARG—LYS—GLU—ARG—D—ALA—ARG (c.p.m.: mean ± S.E.)

| % PWM | Route of Administr. | CONTROLS | PEPTIDE | Δ % |
|---|---|---|---|---|
| 0.00 | oral | 914 ± 336 | 888 ± 97 | − 3 |
| 0.15 | " | 867 ± 291 | 3914 ± 1055 | + 351 |
| 0.31 | " | 2855 ± 1279 | 7076 ± 777 | + 148 |
| 0.62 | " | 1246 ± 549 | 2821 ± 1476 | + 126 |
| 1.25 | " | 681 ± 168 | 657 ± 170 | − 4 |
| 2.50 | " | 727 ± 150 | 634 ± 30 | − 13 |
| 0.00 | i.p. | 1728 ± 501 | 2103 ± 351 | + 22 |
| 0.15 | " | 5352 ± 2925 | 9028 ± 1641 | + 69 |
| 0.31 | " | 3882 ± 1654 | 7027 ± 1059 | + 81 |
| 0.62 | " | 2501 ± 1353 | 5999 ± 3205 | + 140 |
| 1.25 | " | 2334 ± 920 | 4187 ± 842 | + 79 |
| 2.50 | " | 2609 ± 1561 | 4201 ± 2139 | + 61 |

In vitro production of IL-2 by human cells

| TREATMENT | PEPTIDE CONC. (mcg/ml) | IL-2 30' | | after: 60' | |
|---|---|---|---|---|---|
| | | U/ml | Δ % | U/ml | Δ % |
| PBMC | — | 1.0 | — | < 0.8 | — |
| PBMC + ConA | — | 1.45 | — | 1.45 | — |
| GLU—LYS—ARG | 1.0 | 2.3 | + 59 | 1.8 | + 24 |
| ARG—LYS—GLU—ARG—ALA—ARG | 1.0 | 2.3 | + 59 | 2.0 | + 38 |
| ARG—LYS—GLU—ARG—ALA—ARG | 10.0 | 2.0 | + 38 | 1.95 | + 34 |
| ARG—LYS—GLU—D—ALA—ARG | 1.0 | 4.5 | + 210 | 2.5 | + 72 |

| TREATMENT | PEPTIDE CONC. (mcg/ml) | INTERFERON | |
|---|---|---|---|
| | | U/ml | Δ % |
| ConA | — | 5.4 | — |
| ARG—LYS—GLU—ARG—D—ALA—ARG | 1.0 | 5.4 | — |
| ARG—LYS—GLU—ARG—D—ALA—ARG | 10.0 | 6.8 | + 26 |
| ARG—ALA—ARG—ARG—LYS—GLU | 1.0 | 5.5 | + 2 |
| ARG—ALA—ARG—ARG—LYS—GLU | 10.0 | 6.2 | + 15 |
| ARG—ALA—ARG—ARG—LYS—GLU—ARG—ALA—ARG | 1.0 | 5.4 | + 0 |
| ARG—ALA—ARG—ARG—LYS—GLU—ARG—ALA—ARG | 10.0 | 10.0 | + 85 |

Ex-vivo stimulation of mitogen-induced proliferation

The stimulation of mitogen-induce proliferation has been investigated by oral or i.p. administration of the peptides to nude athymic mice (body weight 28 g) at the dosage of 10 mcg/mouse, daily for 5 days, 2 or 6 weeks. The animals were sacrificed 24 hours after the last treatment, and the DNA proliferation was determined as labeled thymidine uptake by the spleen cells. The mitogens used were phytohemoagglutinin (PHA), concanavalin A (ConA) and pokeweed mitogen (PWM).

As it can be seen from the following tables, the in vivo administration of the peptides stimulates the mitogen-induced proliferation, determined ex-vivo.

MITOGEN-INDUCED PROLIFERATION IN NUDE MICE TREATED FOR 5 DAYS WITH 10 mcg/mouse OF THE PEPTIDES BY ORAL ROUTE - c.p.m. (x ± S.E.)

| MITOGEN | % | CONTROLS X ± S.E. | GLU—LYS—ARG X ± S.E. | Δ % | ARG—LYS—GLU—ARG—D—ALA—ARG X ± S.E. | Δ % | ARG—ALA—ARG—ARG—LYS—GLU X ± S.E. | Δ % | ARG—ALA—ARG—ARG—LYS—GLU—ARG—ALA—ARG X ± S.E. | Δ % |
|---|---|---|---|---|---|---|---|---|---|---|
| PHA | 0.000 | 379 ± 43 | 860 ± 145 | +127 | 628 ± 68 | +66 | 442 ± 104 | +17 | 499 ± 4 | +32 |
| | 0.125 | 323 ± 9 | 660 ± 94 | +104 | 800 ± 105 | +148 | 384 ± 3 | +19 | 374 ± 21 | +16 |
| | 0.250 | 490 ± 229 | 953 ± 10 | +94 | 1066 ± 203 | +118 | 617 ± 91 | +26 | 573 ± 63 | +17 |

-continued

MITOGEN-INDUCED PROLIFERATION IN NUDE MICE TREATED FOR 5 DAYS
WITH 10 mcg/mouse OF THE PEPTIDES BY ORAL ROUTE - c.p.m. (x ± S.E.)

| MITO-GEN | % | CONTROLS X ± S.E. | GLU—LYS—ARG X ± S.E. | Δ % | ARG—LYS—GLU—ARG—D—ALA—ARG X ± S.E. | Δ % | ARG—ALA—ARG—ARG—LYS—GLU X ± S.E. | Δ % | ARG—ALA—ARG—ARG—LYS—GLU—ARG—ALA—ARG X ± S.E. | Δ % |
|---|---|---|---|---|---|---|---|---|---|---|
|  | 0.500 | 476 ± 61 | 1435 ± 35 | +202 | 2313 ± 829 | +386 | 827 ± 59 | +74 | 934 ± 432 | +96 |
|  | 1.000 | 675 ± 90 | 2948 ± 395 | +337 | 3922 ± 15 | +48 | 2652 ± 666 | +293 | 622 ± 118 | −8 |
|  | 2.000 | 2937 ± 1931 | 3675 ± 85 | +25 | 2968 ± 143 | +1 | 3266 ± 1469 | +11 | 2741 ± 1679 | −7 |
| PWM | 0.000 | 504 ± 139 | 881 ± 33 | +75 | 1397 ± 106 | +177 | 405 ± 18 | −20 | 421 ± 81 | −17 |
|  | 0.125 | 393 ± 30 | 1981 ± 257 | +404 | 1661 ± 53 | +323 | 588 ± 58 | +50 | 610 ± 3 | +55 |
|  | 0.250 | 633 ± 164 | 2627 ± 691 | +315 | 1788 ± 199 | +182 | 644 ± 112 | +2 | 811 ± 11 | +28 |
|  | 0.500 | 524 ± 9 | 4655 ± 558 | +788 | 2525 ± 323 | +382 | 613 ± 10 | +17 | 1168 ± 50 | +123 |
|  | 1.000 | 569 ± 6 | 4801 ± 1440 | +744 | 2735 ± 412 | +381 | 752 ± 72 | +32 | 930 ± 32 | +63 |
|  | 2.000 | 991 ± 342 | 4993 ± 1223 | +404 | 2511 ± 18 | +153 | 886 ± 189 | −11 | 1151 ± 23 | +16 |
| ConA | 0.000 | 341 ± 23 | 897 ± 25 | +163 | 1080 ± 246 | +217 | 440 ± 41 | +29 | 352 ± 3 | +3 |
|  | 0.312 | 402 ± 57 | 4818 ± 0 | +1099 | 3860 ± 441 | +860 | 559 ± 40 | +39 | 514 ± 3 | +28 |
|  | 0.625 | 450 ± 13 | 11108 ± 252 | +2368 | 5721 ± 194 | +1171 | 1191 ± 92 | +165 | 484 ± 150 | +8 |
|  | 1.250 | 706 ± 99 | 27398 ± 1280 | +3781 | 6493 ± 277 | +883 | 3234 ± 806 | +358 | 694 ± 103 | −2 |
|  | 2.500 | 720 ± 91 | 73703 ± 6790 | +10137 | 5527 ± 1421 | +668 | 4861 ± 720 | +575 | 741 ± 16 | +3 |
|  | 5.000 | 1700 ± 806 | 52567 ± 11504 | +2992 | 4478 ± 743 | +163 | 14857 ± 9644 | +774 | 1783 ± 12 | +5 |

MITOGEN-INDUCED PROLIFERATION IN NUDE
MICE TREATED FOR 2 WEEKS WITH 10 mcg/mouse OF
THE PEPTIDE BY ORAL ROUTE (c.p.m.: mean ± S.E.)

| MITOGEN | % | CONTROLS | GLU—LYS—ARG | Δ % |
|---|---|---|---|---|
| PHA | 0.00 | 4140 ± 196 | 4672 ± 131 | + 13 |
|  | 0.50 | 4201 ± 506 | 6876 ± 963 | + 63 |
|  | 0.75 | 4098 ± 301 | 7740 ± 630 | + 89 |
|  | 1.00 | 4607 ± 533 | 19842 ± 594 | + 383 |
|  | 2.00 | 4470 ± 343 | 35657 ± 619 | + 698 |
| ConA | 0.00 | 4269 ± 587 | 3528 ± 516 | − 18 |
|  | 0.50 | 4272 ± 77 | 113536 ± 17906 | + 2558 |
|  | 0.75 | 3896 ± 384 | 73952 ± 4889 | + 1798 |
|  | 1.00 | 4194 ± 709 | 6805 ± 389 | + 62 |
|  | 2.00 | 1517 ± 362 | 762 ± 240 | − 50 |
| PWM | 0.00 | 1363 ± 162 | 2319 ± 220 | + 70 |
|  | 0.50 | 2074 ± 206 | 22126 ± 2811 | + 967 |
|  | 0.75 | 1990 ± 28 | 21448 ± 717 | + 978 |
|  | 1.00 | 2351 ± 873 | 21919 ± 2506 | + 832 |
|  | 2.00 | 1602 ± 109 | 12816 ± 839 | + 700 |

MITOGEN-INDUCED PROLIFERATION IN NUDE
MICE TREATED FOR 6 WEEKS WITH 10
mcg/mouse OF THE PEPTIDE BY ORAL ROUTE
(c.p.m.: mean ± S.E.)

| MITOGEN | % | CONTROLS | GLU—LYS—ARG | Δ % |
|---|---|---|---|---|
| ConA | 0.00 | 1001 ± 587 | 2671 ± 331 | + 167 |
|  | 0.25 | 3568 ± 71 | 4825 ± 877 | + 35 |
|  | 0.50 | 2670 ± 39 | 5311 ± 1030 | + 99 |
|  | 1.00 | 3103 ± 123 | 7361 ± 404 | + 137 |
|  | 2.00 | 2128 ± 106 | 3141 ± 101 | + 48 |
|  | 4.00 | 853 ± 16 | 959 ± 221 | + 12 |
| PWM | 0.00 | 1228 ± 175 | 3779 ± 1142 | + 208 |
|  | 0.125 | 779 ± 50 | 2264 ± 198 | + 191 |
|  | 0.25 | 1106 ± 167 | 2124 ± 211 | + 92 |
|  | 0.50 | 2322 ± 299 | 2646 ± 141 | + 14 |
|  | 1.00 | 1146 ± 476 | 2616 ± 64 | + 128 |
|  | 2.00 | 898 ± 323 | 2607 ± 584 | + 190 |

MITOGEN-INDUCED PROLIFERATION IN NUDE
MICE TREATED I.P. FOR 6 WEEKS WITH 10
mcg/mouse OF THE PEPTIDE (c.p.m.: mean ± S.E.)

| MITOGEN | % | CONTROLS | GLU—LYS—ARG | Δ % |
|---|---|---|---|---|
| ConA | 0.00 | 2015 ± 159 | 2583 ± 491 | + 28 |
|  | 0.25 | 2084 ± 101 | 6486 ± 388 | + 211 |
|  | 0.50 | 2313 ± 157 | 10099 ± 584 | + 337 |
|  | 1.00 | 3289 ± 133 | 17192 ± 169 | + 423 |
|  | 2.00 | 2498 ± 647 | 10850 ± 1459 | + 334 |
|  | 4.00 | 1525 ± 107 | 2472 ± 901 | + 62 |
| PWM | 0.00 | 1936 ± 150 | 2856 ± 113 | + 48 |
|  | 0.125 | 2464 ± 297 | 3437 ± 914 | + 39 |
|  | 0.25 | 2991 ± 95 | 3955 ± 193 | + 32 |
|  | 0.50 | 2434 ± 188 | 3503 ± 502 | + 44 |
|  | 1.00 | 3177 ± 292 | 3246 ± 860 | + 3 |
|  | 2.00 | 2509 ± 359 | 2453 ± 467 | − 2 |

EXAMPLE 4

Acute Toxicity

The peptides of the invention had a $LD_{50}$ higher than 500 mg/kg i.p. in the mouse.

We claim:

1. A peptide selected from the group consisting of Arg-Lys-Glu-Arg-Ala-Arg, Arg-Lys-Glu-Arg-D-Ala-Arg, Arg-Ala-Arg-Arg-Lys-Glu, Arg-D-Ala-Arg-Arg-Lys-Glu, Arg-Ala-Arg-Arg-Lys-Glu-Arg-Ala-Arg, Arg-Ala-Arg-Glu-Lys-Arg-, Glu-Lys-Arg-Arg-Ala-Arg, Glu-Lys-Arg-Arg-Ala-Arg-Glu-Lys-Arg, and a pharmaceutically acceptable salt thereof.

2. A Peptide according to claim 1 wherein the aminoacids are of the D-, L- or DL series.

3. The peptide, according to claim 1, wherein said salt is the acetate, trifluoroacetate, sulfate, or hydrochloride salt.

4. A pharmaceutical composition having immunostimulating activity comprising as the active principle an effective amount of a peptide selected from the group consisting of Arg-Lys-Glu-Arg-Ala-Arg, Arg-Lys-Glu-Arg-D-Ala-Arg, Arg-Ala-Arg-Arg-Lys-Glu, Arg-D-Ala-Arg-Arg-Lys-Glu, Arg-Ala-Arg-Arg-Lys-Glu-Arg-Ala-Arg, Arg-Ala-Arg-Glu-Lys-Arg, Glu-Lys-Arg-Arg-Ala-Arg, Glu-Lys-Arg-Arg-Ala-Arg-Glu-Lys-Arg and a pharmaceutically acceptable salt thereof in a mixture with an acceptable carrier.

* * * * *